US009782105B2

United States Patent
Yoshino et al.

(10) Patent No.: US 9,782,105 B2
(45) Date of Patent: Oct. 10, 2017

(54) DEVICE FOR MEASURING THE AMOUNT OF WATER IN A SUBJECT'S BODY

(71) Applicant: TERUMO KABUSHIKI KAISHA, Tokyo (JP)

(72) Inventors: Keisuke Yoshino, Tokyo (JP); Kei Honda, Kanagawa (JP); Kosuke Nishio, Kanagawa (JP); Akira Kondou, Kanagawa (JP); Takeshi Tsubouchi, Kanagawa (JP); Miyuki Koyama, Kanagawa (JP)

(73) Assignee: Terumo Kabushiki Kaisha, Tokyo (JP)

( * ) Notice: Subject to any disclaimer, the term of this patent is extended or adjusted under 35 U.S.C. 154(b) by 94 days.

(21) Appl. No.: 14/622,222

(22) Filed: Feb. 13, 2015

(65) Prior Publication Data
US 2015/0150479 A1    Jun. 4, 2015

Related U.S. Application Data

(63) Continuation of application No. PCT/JP2012/005152, filed on Aug. 14, 2012.

(51) Int. Cl.
*A61B 5/053*    (2006.01)
*A61B 5/00*    (2006.01)
*G01N 33/18*    (2006.01)

(52) U.S. Cl.
CPC .......... *A61B 5/0537* (2013.01); *A61B 5/4875* (2013.01); *G01N 33/18* (2013.01);
(Continued)

(58) Field of Classification Search
CPC .... A61B 2560/0418; A61B 2560/0425; A61B 5/0537; A61B 5/4875; A61H 23/00–2023/029
(Continued)

(56) References Cited

U.S. PATENT DOCUMENTS 1,377,140 A * 5/1921 North ..................... A61H 7/005
                                                    601/108
4,604,993 A * 8/1986 Moriwaki .......... A61H 23/0263
                                                    601/18
(Continued)

FOREIGN PATENT DOCUMENTS

EP    1543768    6/2005
GB    2133990    8/1984
(Continued)

OTHER PUBLICATIONS

Official Action and English Translation for Japan Patent Application No. 2014-530392, dated Feb. 19, 2016, 4 pages.
(Continued)

*Primary Examiner* — Michael C Stout
(74) *Attorney, Agent, or Firm* — Sheridan Ross P.C.

(57) ABSTRACT

A device (100) for measuring the amount of water in a subject's body includes a main body part (110) formed in a linear shape and an insertion part (120) extending in a curved shape from one end of the main body part (100). The insertion part (120) includes a tip side insertion part (120-2) having a tip surface (122) to which a sensor unit (121) is fixed and a base end side insertion part (120-1), wherein the sensor unit (121) is brought into contact with a body surface of a subject through a slide mechanism. A protective member (651) liquid-tightly covers the slide mechanism between the tip side insertion part (120-2) and a base end side insertion part (120-1). The protective member (651) smoothly connects the outer peripheral surface of the tip side insertion part (120-2) and the outer peripheral surface of the base end side insertion part (120-1).

20 Claims, 13 Drawing Sheets

(52) U.S. Cl.
CPC . *A61B 2560/0418* (2013.01); *A61B 2562/029* (2013.01); *A61B 2562/247* (2013.01)

(58) Field of Classification Search
USPC ................ 600/372, 382–397, 547, 546, 548
See application file for complete search history.

(56) References Cited

U.S. PATENT DOCUMENTS

| | | | | |
|---|---|---|---|---|
| 4,958,628 | A * | 9/1990 | Iwamoto | A61H 23/0263 601/72 |
| 5,193,528 | A * | 3/1993 | Iwamoto | A61H 23/0263 16/429 |
| 5,755,672 | A | 5/1998 | Arai et al. | |
| 6,196,990 | B1 * | 3/2001 | Zicherman | A61H 23/0254 604/29 |
| 6,491,647 | B1 * | 12/2002 | Bridger | A61B 5/021 128/900 |
| 6,789,936 | B1 * | 9/2004 | Kraus | G01J 5/0022 374/121 |
| 2004/0077969 | A1 * | 4/2004 | Onda | A61B 5/0537 600/547 |
| 2005/0159655 | A1 * | 7/2005 | Kao | A61B 5/442 600/306 |
| 2005/0240102 | A1 * | 10/2005 | Rachlin | A61B 8/10 600/437 |
| 2007/0100200 | A1 * | 5/2007 | Suzuki | A61B 1/00151 600/101 |
| 2007/0106171 | A1 * | 5/2007 | Li | A61H 39/02 600/548 |
| 2007/0173892 | A1 * | 7/2007 | Fleischer | A61B 5/02405 607/2 |
| 2008/0146890 | A1 * | 6/2008 | LeBoeuf | A61B 5/0059 600/300 |
| 2013/0274566 | A1 | 10/2013 | Koyama et al. | |

FOREIGN PATENT DOCUMENTS

| | | |
|---|---|---|
| JP | S59-139261 | 8/1984 |
| JP | H09-206282 | 8/1997 |
| JP | 2000-051153 | 2/2000 |
| JP | 2005-205041 | 8/2005 |
| JP | 3120546 | 4/2006 |
| JP | 2009-153727 | 7/2009 |
| JP | 4417841 | 2/2010 |
| WO | WO 2008/132714 | 11/2008 |
| WO | WO 2012/042878 | 4/2012 |
| WO | WO 2012/056634 | 5/2012 |

OTHER PUBLICATIONS

Extended Search Report for European Patent Application No. 12891423.1, dated Feb. 8, 2016, 8 pages.
Official Action (1st) and English Translation for Chinese Patent Application No. 201280074419.0, date unknown, 8 pages.
Official Action (2nd) and English Translation for Chinese Patent Application No. 201280074419.0, date unknown, 8 pages.

* cited by examiner

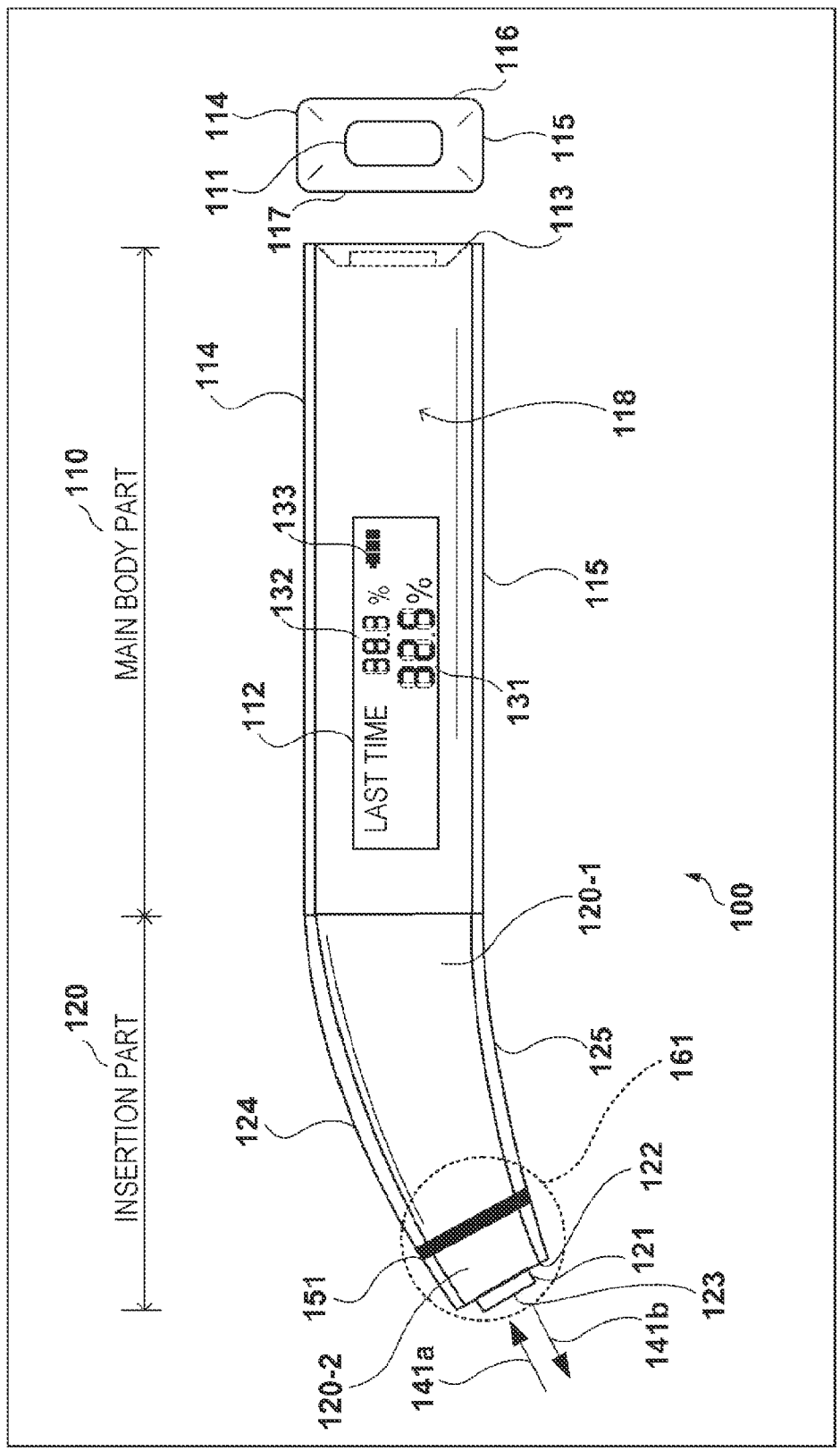

DEVICE FOR MEASURING THE AMOUNT OF WATER IN A SUBJECT'S BODY

CROSS REFERENCE TO RELATED APPLICATION

The present application is a Continuation of and claims the benefits of and priority to, under 35 U.S.C. §120, PCT Application Serial No. PCT/JP2012/005152, filed Aug. 14, 2012, entitled "Body Water Meter," which is incorporated herein by reference for all that it teaches and for all purposes.

TECHNICAL FIELD

The embodiments described herein generally relate to devices for measuring the amount of water in a subject's body.

BACKGROUND

Measuring the amount of water in a subject's body is essential for diagnosing and for treating medical conditions. Dehydration in a living body is a pathological condition in which water is reduced and often occurs when a person is exercising or when the temperature is high because a lot of water is excreted from the body by sweating to reduce an elevated body temperature. Elderly people are more likely to experience dehydration than general healthy people because of deterioration in the water retention ability in the body.

Generally, when water, in a living body, is reduced by 3% or more of the body weight, body temperature regulation is disturbed. This disturbance of body temperature regulation causes the body temperature to increase, and then water in the living body is further reduced. In other words, a vicious cycle of dehydration is created, which leads to, at last, a pathological condition called heat illness. Heat illness includes conditions such as heat cramp, heat exhaustion, and heatstroke. In some cases, all the organs in the body are affected by heat illness. Thus, it is important to accurately measure the amount of water in the body to avoid the risk of a heat illness.

The armpit is generally a suitable region of the body to obtaining accurately the amount of water in the subject's body. A device to measure the amount of water in a person's body may have a sensor unit with electrodes arranged thereon that measures the capacitance between the electrodes while applying the sensor unit to the armpit to calculate the amount of water in the subject's body.

FIGS. 12 and 12a show diagrams illustrating an example of a device 1200 for measuring the amount of water in a subject's body. As illustrated in FIGS. 12 and 12a, the device 1200 is provided with a main body part 1210 and an insertion part 1220. The main body part 1210 can be grasped, by a measurer (e.g., a nurse or care giver). The main body part 1210 can be formed in a linear shape. A display unit 1212 may be arranged on the surface of a casing of the main body part 1210 to display, for example, a measurement result 1231 thereon. The insertion part 1220 can be inserted into the armpit as the insertion part 1220 extends from one end of the main body part 1210 and can be gently curved relative to the main body part 1210.

A sensor unit 1221 can be slidably supported on a tip surface 1222 of the insertion part 1220. The sensor unit 1221 may include a sensor head 1223, which has a surface substantially parallel to the tip surface 1222. The sensor unit 1221 is biased in a direction indicated by an arrow 1241b, to gain a pressing force for ensuring close contact between the sensor head 1223 and the skin of a subject. When the sensor head 1223 is pressed against the skin of the armpit of a subject, the sensor unit 1221 slides in a direction indicated by an arrow 1241a by a predetermined distance and measurement is started accordingly.

SUMMARY

The configuration of the device 1200 includes an opening for allowing the sensor unit 1221 to slide in the direction indicated by the arrow 1241a. The opening can create problems with the device 1200. FIG. 12b is a diagram illustrating a cross-sectional configuration of a tip region 1250 of the insertion part 1220 including the sensor unit 1221.

As illustrated in FIG. 12b a cavity of the opening 1251 is larger than the sensor head 1223 of the sensor unit 1221. Thus, a gap 1252 is formed between the side surface of the sensor unit 1221 and the inner wall surface of the opening 1251. This opening 1252 enables the sensor unit 1221 to smoothly slide.

Unfortunately, the gap 1252, between the side surface of the sensor unit 1221 and the inner wall surface of the opening 1251, can collect unwanted liquid (e.g., alcohol used for wiping off dirt on the sensor unit 1221), which can enter the inside of the device 1200. The collected water may cause failure of the device 1200.

Further, dust, dirt and other ditritus, for example, a piece of skin inadvertently adhered to the device 1200 during measurement, can accumulate inside the device through the gap 1252. This accumulated debris, may cause failure of the device 1200 or can cause subsequent patients to incur an infection.

The embodiments presented herein have been made in view of the above problems and an object thereof is to improve the waterproof and antifouling properties in a device for measuring the amount of water in a subject's body that has a slidable sensor unit.

Solution to the Problem

To achieve the above object, a device for measuring the amount of water in a subject's body according to embodiments has the following configuration. Specifically, the device for measuring the amount of water in a subject's body includes a main body part formed in a linear shape and an insertion part extending in a curved shape from one end of the main body part. The insertion part includes: a tip side insertion part having a tip surface to which a sensor unit is fixed, wherein the sensor unit is brought into contact with a body surface of a subject to measure data regarding water in a subject's body; a base end side insertion part supporting the tip side insertion part through a slide mechanism, wherein the slide mechanism allows the tip side insertion part to slide in a direction substantially perpendicular to the tip surface; and a protective member that liquid tightly covers or seals the slide mechanism between the tip side insertion part and the base end side insertion part, wherein the protective member smoothly connects an outer peripheral surface of the tip side insertion part and an outer peripheral surface of the base end side insertion part.

Advantageous Effects of the Embodiments

The embodiments make it possible to improve the waterproof and antifouling properties in a device for measuring the amount of water in a subject's body that has a slidable sensor unit.

The other features and advantages of the embodiments will become apparent from the following description with reference to the accompanying drawings. Identical reference numerals designate identical or similar elements throughout the accompanying drawings.

BRIEF DESCRIPTION OF THE DRAWINGS

The accompanying drawings a constitute a part of the Specification, illustrate the embodiments described herein, and are used for explaining and describing the embodiments provided herein.

FIG. 1A is a diagram illustrating a configuration of an embodiment of a device for measuring the amount of water in a subject's body.

DETAILED DESCRIPTION

Figure 1B:
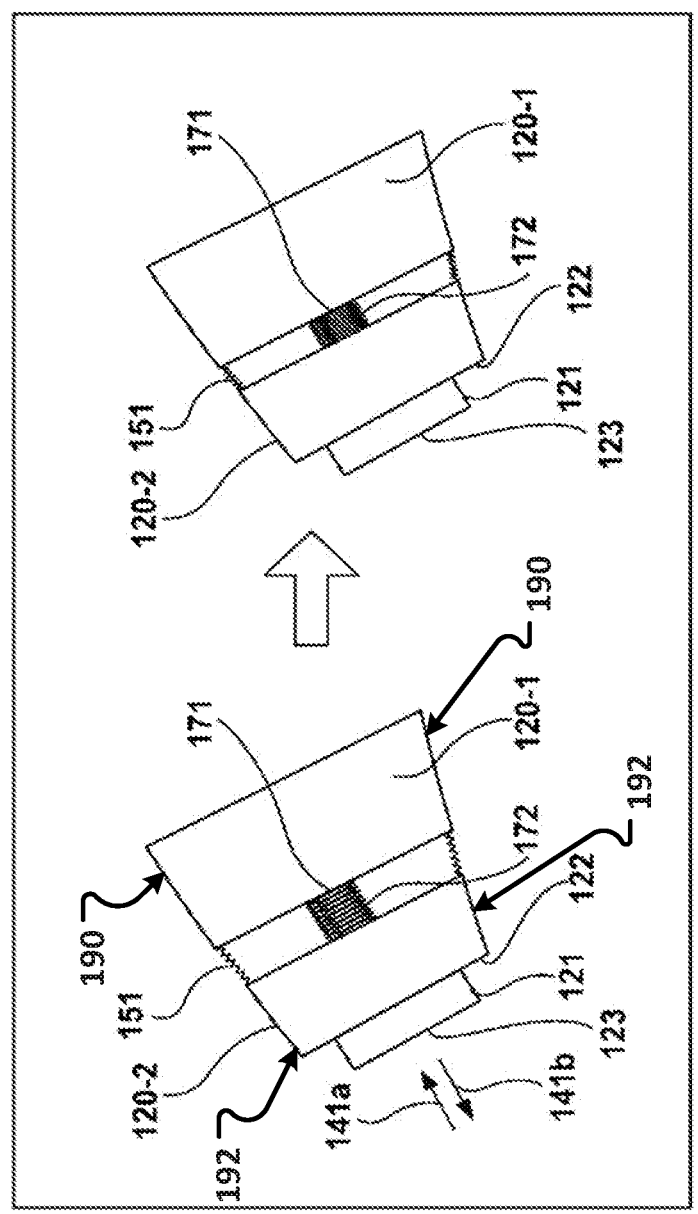
FIG. 1B is a diagram illustrating the configuration of an embodiment of a tip region of the device for measuring the amount of water in a subject's body.

Hereinbelow, embodiments will be described with reference to the drawings. The embodiments described below are exemplary and, therefore, have technically various limitations. However, the scope of the claims is not limited to these embodiments.

1. Configuration of a Device for Measuring Amount of Water in Subject's Body

FIG. 1A is a diagram illustrating an embodiment of a device 100. The device 100 allows a sensor unit to make contact with the skin of the armpit, which is a body surface of a subject, to detect a physical characteristic corresponding to an electric signal supplied in the sensor unit, thereby, by evaluating the electric signal, the device detects the amount of water in the subject's body. The device 100 can measure the capacitance of a subject, as the physical characteristic (which helps determine water in the body), to detect the degree of wetness of the skin of the armpit and, using this information, calculates the amount of water in the subject's body.

As illustrated in FIG. 1A, the device 100 includes a main body part 110 and an insertion part 120 which extends in a curved shape from one end of the main body part 110. The main body part 110 has an upper surface 114, a lower surface 115, and side surfaces 116, 117. The surfaces 114, 115, 116 and/or 117 can be formed substantially parallel to a long-axis direction (not illustrated), and create a main body part 110 which has a linear shape. Various user interfaces can be arranged on the surfaces 114, 115, 116 and/or 117 of a casing of the main body part 110. An electronic circuit for calculating the amount of water in a subject's body is housed inside the casing.

In the example of FIG. 1A, a power switch 111 and a display unit 112 are illustrated as the user interfaces. The power switch 111 is arranged on a recess of a rear end surface 113 of the main body part 110. Arranging the power switch 111 on the recess in this manner makes it possible to prevent inadvertent operation of the power switch 111. When the power switch 111 is turned on, power is supplied from a power supply unit 211 (FIG. 2, described below) to each unit of the device 100 and the device 100 is started. Accordingly, the device 100 is brought into an operating state by depressing the power switch 111.

The display unit 112 can be arranged at a position slightly shifted toward the front side, of the main body part 110 (i.e., from the center in the long-axis direction on the side surface 117), to prevent the display unit 112 from being completely covered with a hand of a measurer when the measurer grasps a grasping region 118. Thus, the display unit 112 is visible to read a measurement of the amount of water in a subject's body using the device 100 (even when a user grasps the devices 100).

A most recent measurement result 131, of the amount of water in the subject's body, is displayed on the display unit 112. The next most recent measurement result 132 is also displayed together with the most recent measurement result 131 as reference. A remaining amount of a battery life (for the power supply unit 211 of FIG. 2) is also displayed on a battery display part 133. When an invalid measurement result is obtained or a measurement error is detected, "E" is displayed on the display unit 112 to notify a measurer of the invalid measurement result or the measurement error. Characters and the like on the display unit 112 are displayed by defining the upper surface 114 of the main body part 110 as the upper side and the lower surface 115 thereof as the lower side.

The insertion part 120 of the device 100 can have a curved upper surface 124 and a curved lower surface 125 and may be gently curved downward as a whole relative to the main body part 110.

A sensor unit 121 may be fixed to a tip surface 122 of the insertion part 120. The sensor unit 121 can include a sensor head 123, which has a surface substantially parallel to the tip surface 122.

The insertion part 120 can be separated into a base end side insertion part 120-1 which is connected to the main body part 110 and a tip side insertion part 120-2 to which the sensor unit 121 is fixed. The tip side insertion part 120-2 is biased (e.g., with a biasing force of approximately 150 gf) in a direction indicated by an arrow 141b by an elastic member, for example, a spring to gain a pressing force for ensuring close contact between the sensor head 123 and the skin. When the sensor head 123 is pressed against the skin of the armpit of a subject, the entire tip side insertion part 120-2 slides in a direction indicated by an arrow 141a (the direction substantially perpendicular to the tip surface 122, or the normal direction of the tip surface 122) by a predetermined amount (e.g., 1 mm to 10 mm, and 3 mm in the present embodiment). A measurement may be started accordingly (hereinbelow, the direction indicated by the arrow 141a is referred to as "slide direction") after the sensor head 123 makes contact with the skin.

The outer peripheral surface 190 (shown in FIG. 1B) of the base end side insertion part 120-1 and the outer peripheral surface 192 (shown in FIG. 1B) of the tip side insertion part 120-2 are connected to each other through a protective member 151, which is composed of an elastic member (a bellows-like elastic member), which is extendable and contractable in the slid direction (a detailed configuration of a tip region (the region indicated by a dotted line 161) of the device 100 including the protective member 151 will be described below). The outer peripheral surface 190 is the outer most surface that faces radial outward on the exterior of the base end side insertion part 120-1. The outer peripheral surface 192 is the outer most surface that faces radial outward on the exterior of the tip side insertion part 120-2.

With such a configuration, when the sensor head 123 is detected to be pressed against the armpit of a subject, after a measurer turns on the power switch 111 to bring the device 100 into an operating state, measurement of the amount of water in the subject's body is started. Alternatively, when the sensor head 123 is detected to be pressed against the armpit of a subject with a predetermined load (e.g., 20 gf to 200 gf, more preferably 100 gf to 190 gf, and 150 gf in the present embodiment) and after a measurer turns on the power switch 111 to bring the device 100 into an operating state, measurement of the amount of water in the subject's body is started. Such a device structure enables the degree of close contact between the sensor head 123 and the armpit during the measurement to be constant.

2. Configuration of Tip Region of Device for Measuring Amount of Water in Subject's Body Next, the detailed configuration of the tip region (the region indicated by the dotted line 161 of FIG. 1A) of the device 100 will be described. FIG. 1B is a diagram illustrating the configuration of the tip region of the device 100. FIG. 1B illustrates the configuration of the inside of a region covered with the protective member 151.

As illustrated in FIG. 1B, the protective member 151 is disposed along the outer peripheral surface of the base end side insertion part 120-1 and the outer peripheral surface of the tip side insertion part 120-2. The protective member 151 smoothly connects the outer peripheral surface of the base end side insertion part 120-1 and the outer peripheral surface of the tip side insertion part 120-2, so as to be integrally configured in the insertion part 120, which is gently curved downward relative to the main body part 110 and tapered toward the tip thereof.

The integrated configuration between the outer peripheral surface of the base end side insertion part 120-1 and the outer peripheral surface of the tip side insertion part 120-2 can enable a measurer to perform easily a wiping operation when wiping off dirt adhered to the insertion part 120.

A support member 171 can be arranged inside the protective member 151 to support slidably the tip side insertion part 120-2. Further, a force-producing or elastic member 172, for example, a spring, can be arranged to bias the tip side insertion part 120-2 in the direction indicated by the arrow 141b.

Arranging the mechanism (slide mechanism) for allowing the tip side insertion part 120-2 to slide inside the protective member 151 makes it possible to prevent liquid from entering the device 100 through the slide mechanism. That is, it is possible to improve the waterproof and antifouling properties of the device 100.

The protective member 151 is extendable and contractable in the slide direction. When the sensor head 123 is pressed against the skin of the armpit of a subject and further pressed against a biasing force of the elastic member 172, the tip side insertion part 120-2 slides in the direction indicated by the arrow 141a. Accordingly, the protective member 151 is compressed in the slide direction (refer to the right side in the drawing).

The protective member 151, which is extendable and contractable in the slide direction prevents the protective member 151 from disturbing the slide operation of the tip side insertion part 120-2. Thus, a measurer can perform the pressing operation with a constant pressing force. Examples of a preferred material of the protective member 151 can include, but are not limited to, elastic members, such as elastomers (such as a silicone elastomer, polyurethane elastomer, or styrene elastomer), polyolefins (such as polyethylene), etc. Further, to give the protective member 151 an antifouling property, the protective member 151 may be coated with a fluorine resin having a trifluoromethyl group (—CF3) as a functional group or like coating.

The configuration in which the insertion part 120 is separated into the base end side insertion part 120-1 and the tip side insertion part 120-2, and the slide mechanism is disposed between the base end side insertion part 120-1 and the tip side insertion part 120-2 further has the following advantages described hereinafter.

Figure 12:
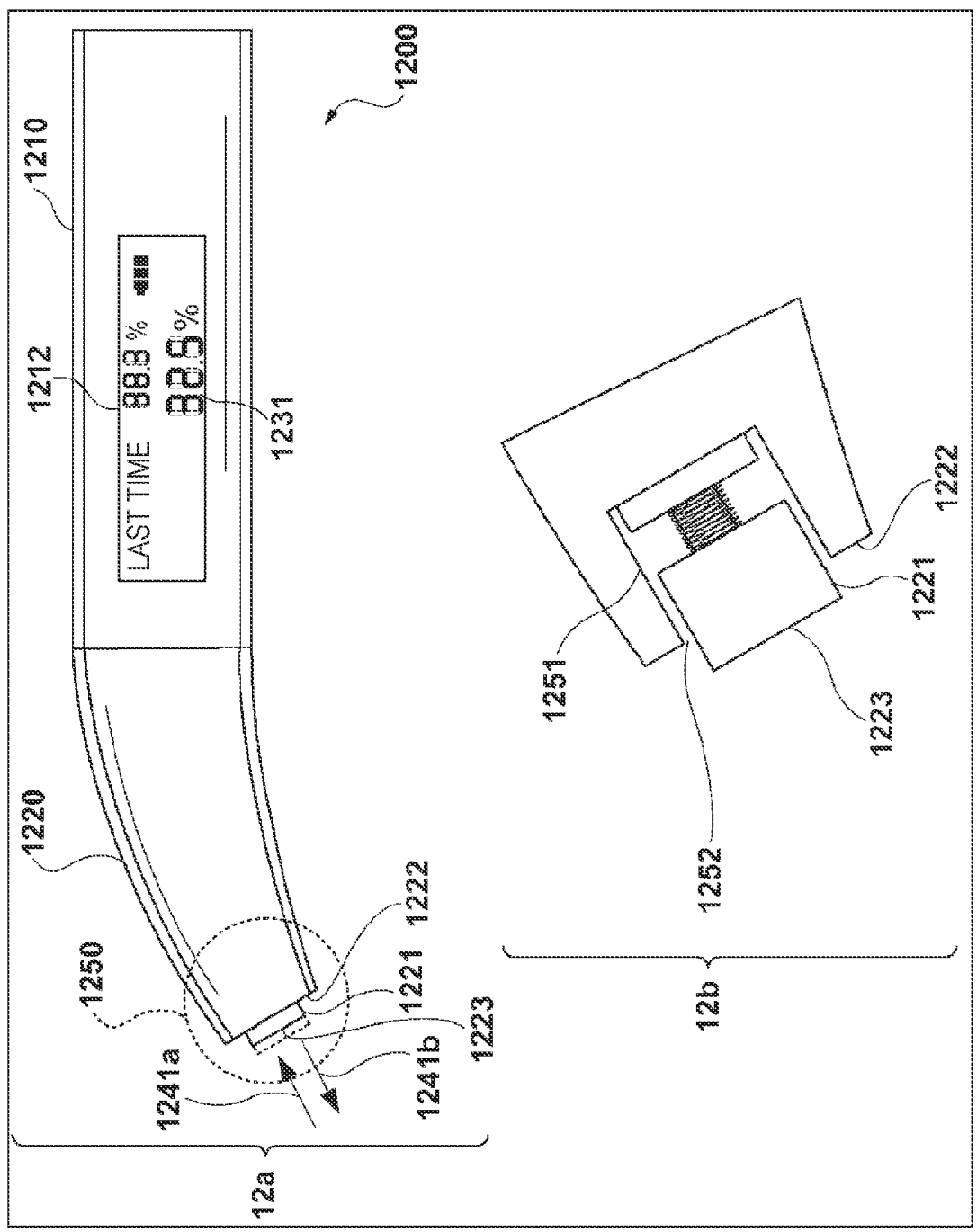
FIG. 12 is a diagram illustrating a configuration of a device for measuring the amount of water in a subject's body and the configuration of a tip region thereof.

As an example, the advantages will be described with a comparison to a device 1200 in which a protective member is arranged between a tip surface 1222 and a sensor unit 1221 for measuring the amount of water in a subject's body as illustrated in FIG. 12, which includes a slide mechanism disposed between an insertion part 1220 and the sensor unit 1221.

In the configuration shown in FIG. 12, one end of the protective member is connected to the tip surface 1222 and the other end thereof is connected to the side surface of the sensor unit 1221. As is apparent from FIG. 12, a region exposed from the insertion part 1220 in the side surface of the sensor unit 1221 is small. Further, a region in the tip surface 1222, forming an opening 1251, is also small. That is, it is assumed that connecting the protective member in the device 1200, illustrated in FIG. 12, makes manufacture of the device difficult because the regions to which both ends of the protective member can be connected are limited.

On the other hand, in the device 100, it is possible to ensure a large region to which the protective member can be connected. Thus, the device 100 has an advantage of easy attachment of the protective member 151 in the manufacturing process.

Further, when the protective member, shown in FIG. 12, is connected to the device 1200 having the sensor unit 1221, which is smaller than the tip surface 1222, as illustrated in FIG. 12, the protective member is arranged in an inclined manner. That is, an extension/contraction direction of the protective member is not aligned with a slide direction of the sensor unit 1221. As a result, an elastic force of the protective member is nonuniform in the slide direction and affects a pressing force of the sensor unit 1221.

On the other hand, the device 100 is capable of achieving an elastic force that is uniform in the slide direction. Thus, it is possible to eliminate the influence of the elastic force of the protective member 151 on the pressing force in the slide direction.

Figure 2:
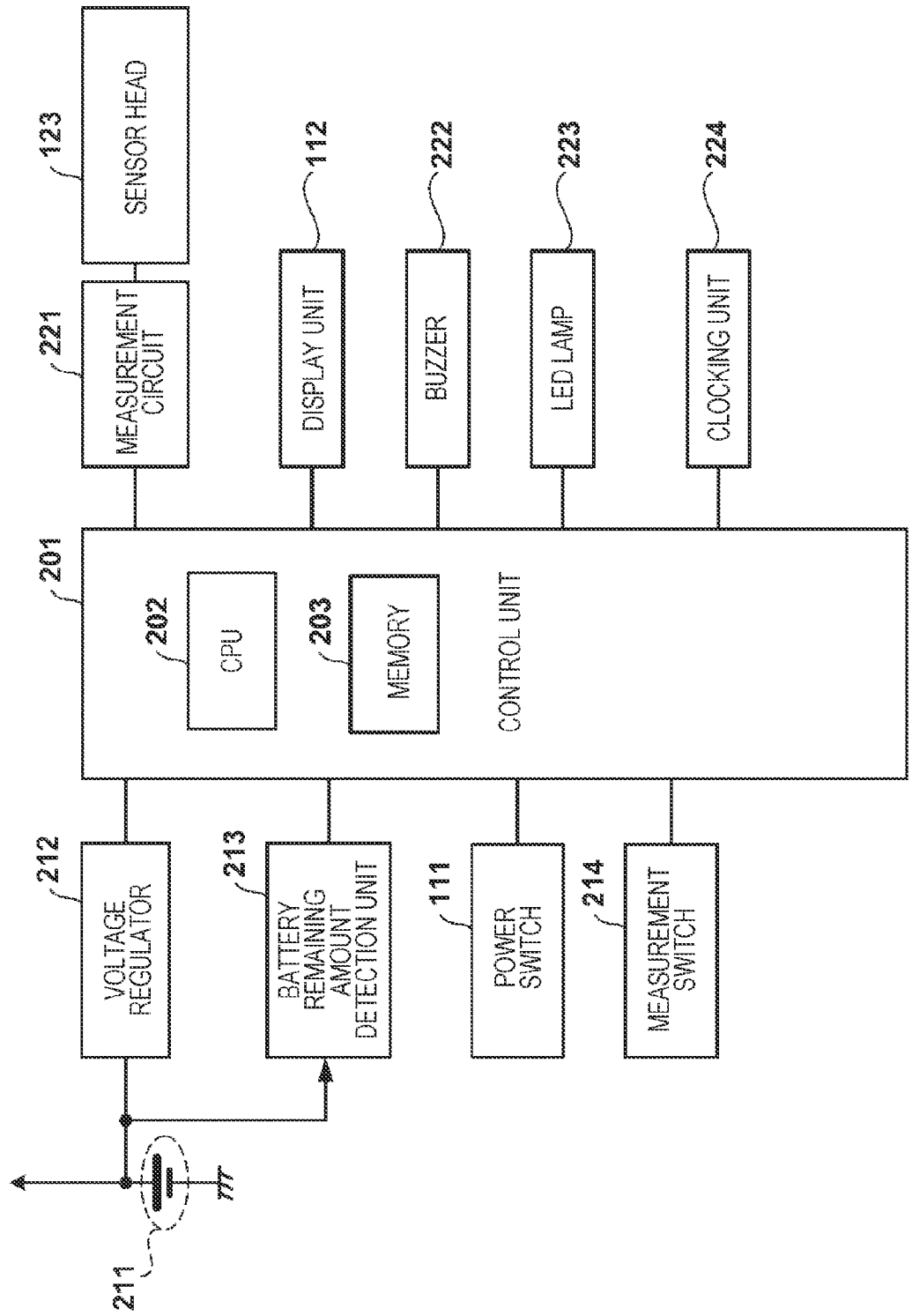
FIG. 2 is a diagram illustrating a functional configuration of an embodiment of the device for measuring the amount of water in a subject's body.

3. Functional Configuration of Device for Measuring Amount of Water in Subject's Body Next, a functional configuration of the device 100 will be described. FIG. 2 is a diagram illustrating the functional configuration of the device 100. In FIG. 2, a control unit 201 includes a CPU 202 and a memory 203. The CPU 202 executes programs stored in the memory 203 to perform various controls in the device 100.

Figure 4:
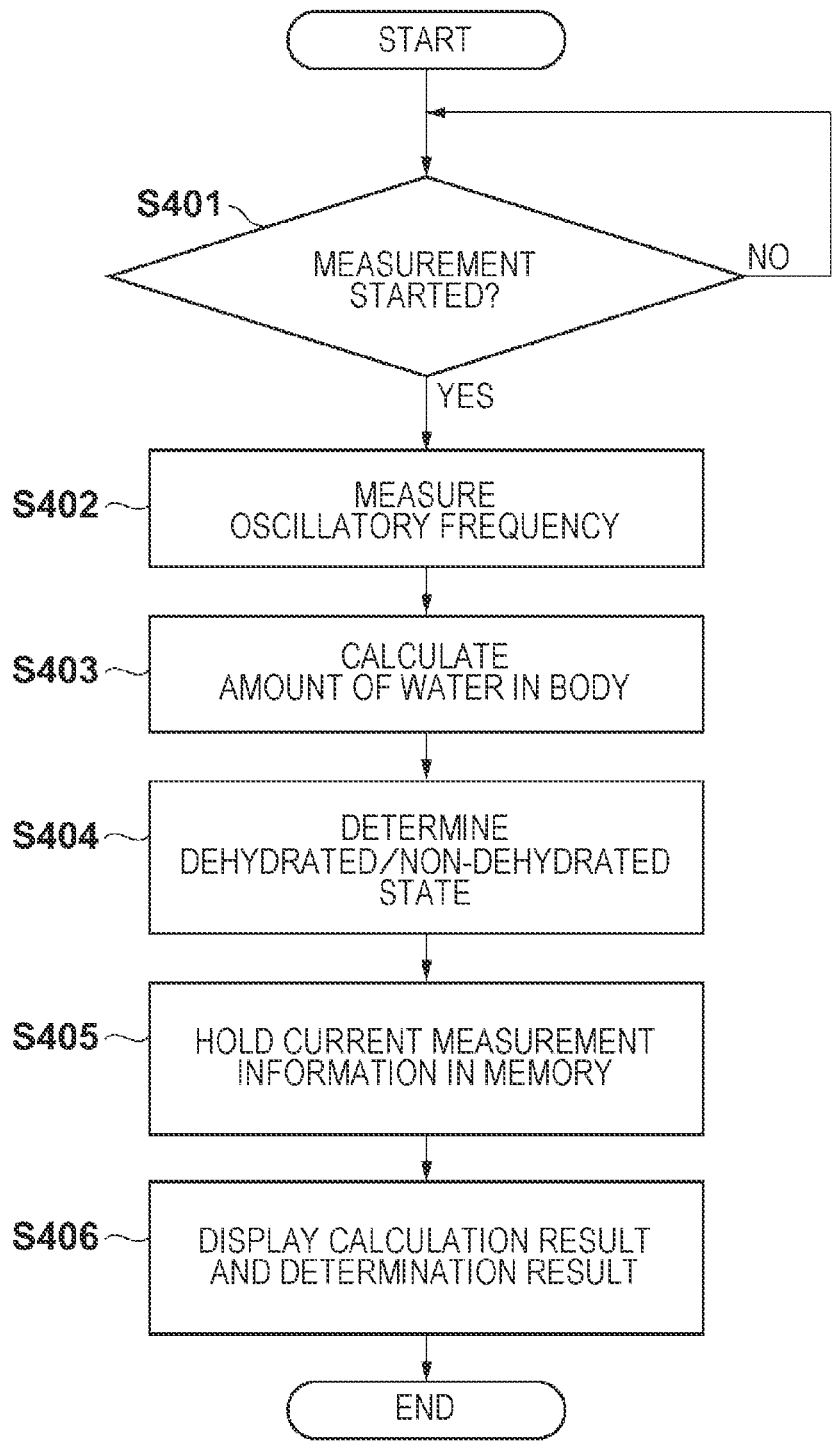
FIG. 4 is a diagram for explaining an operation of an embodiment of the device for measuring the amount of water in a subject's body.

For example, the CPU 202 performs display control for the display unit 112, drive control for a buzzer 222 and an LED lamp 223, and measurement of the amount of water in a subject's body (e.g. measurement of capacitance), which will be described below with reference to a flowchart of FIG. 4. The memory 203 includes a nonvolatile memory and a volatile memory. The nonvolatile memory can be used as a program memory and the volatile memory can be used as an operation memory of the CPU 202.

The power supply unit 211 may include a replaceable battery or a rechargeable battery that supplies power to each unit of the device 100. A voltage regulator 212 can supply a constant voltage (e.g., 2.3 V) to the control unit 201 and the like. A battery life detection unit 213 detects the amount of life remaining in the battery on the basis of a voltage value supplied from the power supply unit 211 and notifies the control unit 201 of a result of the detection. The control unit 201 controls display of the battery display part 133 on the basis of a battery life detection signal from the battery life detection unit 213.

When the power switch 111 is depressed, power can be supplied from the power supply unit 211 to each unit in the device 100, when the device 100 is started. Then, upon detecting that the depression of the power switch 111, by a measurer, has been continued for one second or more, the control unit 201 maintains the power supplied from the power supply unit 211 to each unit to bring the device 100 into an operating state. As described above, a measurement switch 214 is turned on simultaneously with the start of the power supplied from the power supply unit 211. The control unit 201 starts measurement of the amount of body water when the tip side insertion part 120-2 is pressed in the direction indicated by the arrow 141*a* by at least a predetermined amount of force and finishes the measurement when the on state of the measurement switch 214 has continued for at least a predetermined time (e.g., two seconds). To prevent the consumption of power from the power supply unit 211, when measurement is not started after a predetermined amount of time (e.g., two minutes) from the transition of the device 100 to the operating state, the control unit 201 can automatically shift the device 100 to a power-off state.

Figure 3:
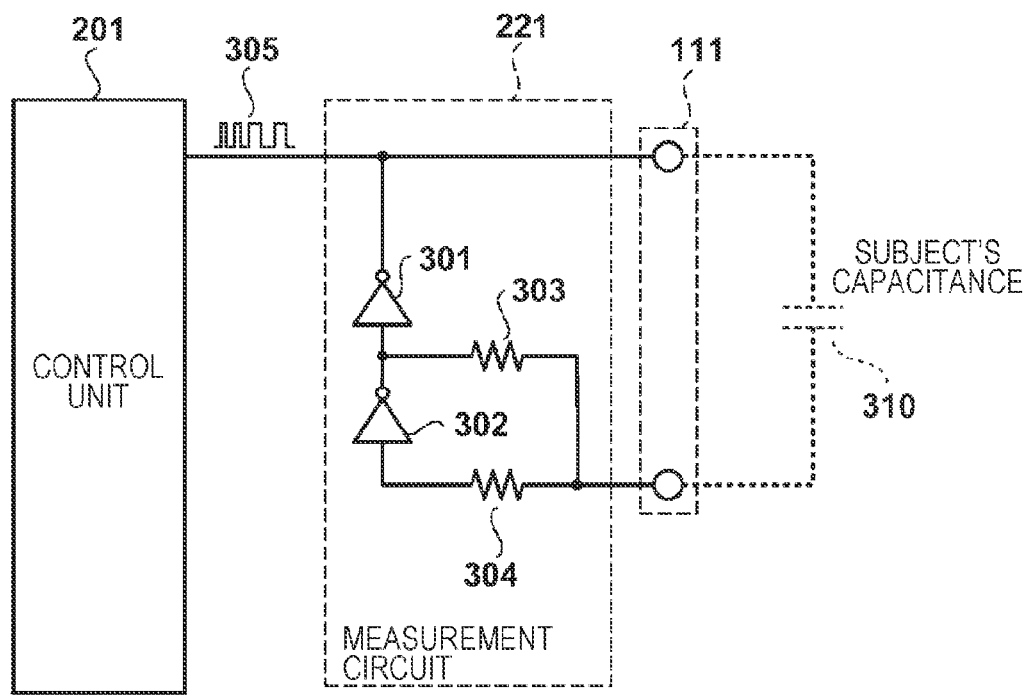
FIG. 3 is a diagram illustrating an example of the configuration of an embodiment of a measurement circuit of the device for measuring the amount of water in a subject's body.

A measurement circuit 221 can be connected to the sensor head 123 and measures the capacitance of the subject's body. FIG. 3 is a diagram illustrating an example of the configuration of the measurement circuit 221. As illustrated in FIG. 3, a CR oscillation circuit is formed from inverters 301, 302, resistors 303, 304, and a subject's capacitance 310. The oscillatory frequency of an output signal 305 varies depending on the subject's capacitance 310. Thus, the control unit 201 measures the frequency of the output signal 305 to calculate the subject's capacitance 310. The sensor head 123 can include two comb-shaped electrodes which are arranged in such a manner that comb teeth of the respective electrodes are alternately arranged.

Referring back to FIG. 2, the display unit 112 controls the display, as described with reference to FIG. 1A, under the control of the control unit 201. The buzzer 222 can sound either when a measurement is started, in response to pressing the tip side insertion part 120-2, or when the measurement of the amount of water in a subject's body has been completed, and notifies a measurer of the start or completion of the measurement. The LED lamp 223 can also perform the same notifications as performed by the buzzer 222. That is, the LED lamp 223 may be lit either when measurement is started in response to pressing the tip side insertion part 120-2 or measurement of the amount of water in a subject's body has been completed, and notifies a measurer of the start or completion of the measurement. A clocking unit 224 operates by receiving power from the power supply unit 211, even in a power-off state, and notifies the control unit 201 of time in an operating state.

4. Operation of Device for Measuring Amount of Water in Subject's Body

An operation of the device 100 having the above configuration will be described with reference to the flowchart of FIG. 4.

In step S401, the control unit 201 detects an instruction of starting measurement. A state of the measurement switch 214 can be monitored by a control unit 201. When an on state of the measurement switch 214 has continued for a predetermined amount of time, e.g., two seconds or more, the instruction of starting measurement is determined to be detected by the control unit 201. Upon detecting the instruction of starting measurement, the control unit 201 measures the oscillatory frequency of the output signal 305 from the measurement circuit 221, in step S402.

In step S403, the amount of water in a subject's body is calculated on the basis of the oscillatory frequency of the output signal 305 measured in step S402.

In step S404, whether the subject is in a dehydrated state is determined on the basis of whether the amount of water in the subject's body calculated in step S403, exceeds a predetermined threshold. The threshold in this case is desirably a value corresponding to, for example, 35% when defining water as 100% and air as 0%.

In step S405, the current measurement information can be stored in the memory 203 by the control unit 201.

Figure 5:
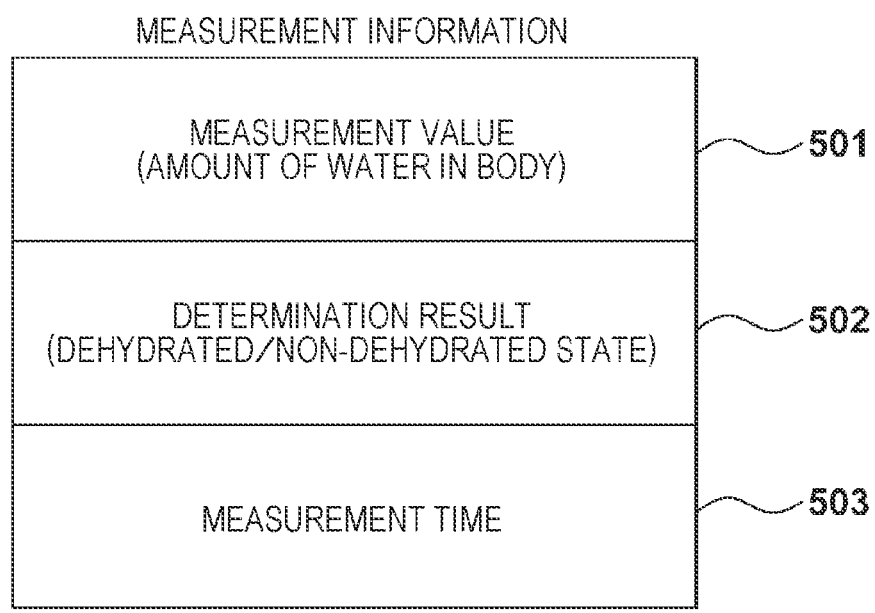
FIG. 5 is a diagram illustrating a data configuration of an embodiment of measurement information.

FIG. 5 is a diagram illustrating an embodiment of a data configuration of measurement information stored in the memory 203. In FIG. 5, a measurement value 501 is the amount of water in the subject's body calculated by the current or most recent measurement. A determination result 502 is information indicating whether the subject is in a dehydrated state or non-dehydrated state, which has been determined, in step S404, with respect to the amount of water in the subject's body calculated in the most recent or current measurement. A measurement time 503 is information indicating a time (i.e., a time of day and/or date), notified or determined from the clocking unit 224, for the most recent or current measurement. The measurement time 503 is, for example, a time reported or notified from the clocking unit 224 at the point when the measurement is performed in step S402.

In step S406, the amount of water in the subject's body, calculated for the most recent or current measurement, is displayed on the display unit 112. At this time, the display is modified or generated to display a determination result of whether the subject is in a dehydrated state or non-dehydrated state (e.g., the amount of water in the subject's body is displayed in red when the subject is in a dehydrated state and in blue when the subject is in a non-dehydrated state).

As is apparent from the above description, the device 100 can include the insertion part 120, which is separated into the base end side insertion part 120-1 and the tip side insertion part 120-2, and the slide mechanism disposed between the base end side insertion part 120-1 and the tip side insertion part 120-2. Further, the outer peripheral surface of the base end side insertion part 120-1 and the outer peripheral surface of the tip side insertion part 120-2 are smoothly connected to each other by the protective member 151, which is extendable and contractable in the slide direction to thereby liquid-tightly cover the slide mechanism.

Accordingly, it is possible to improve the waterproof and antifouling properties of the device 100. Further, even when dirt is adhered to the insertion part 120, it is possible to easily wipe off the dirt. Further, the protective member never obstructs the slide operation. Thus, a measurer can perform a pressing operation with a constant pressing force.

Figure 6:
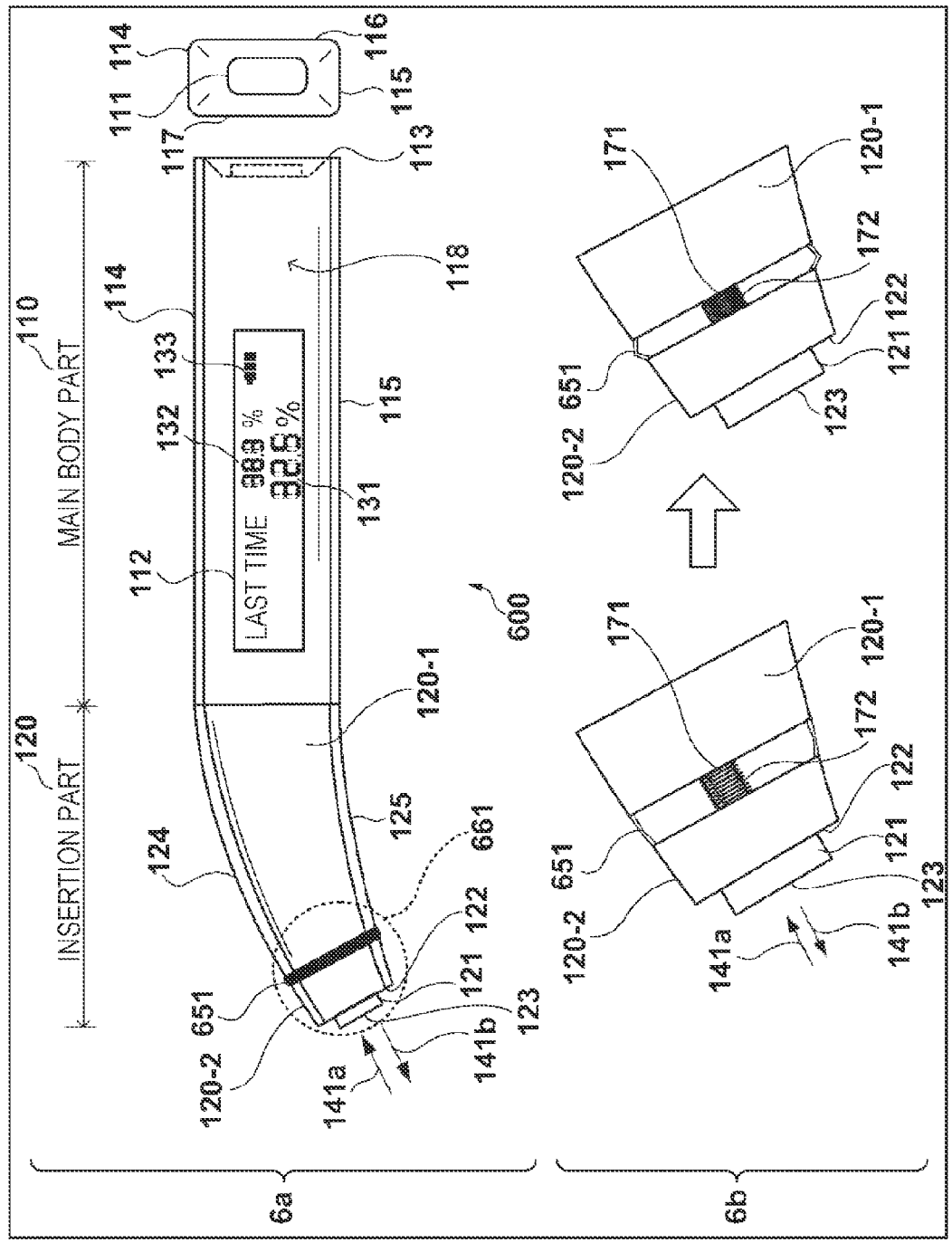
FIG. 6 is a diagram illustrating a configuration of an embodiment of a device for measuring the amount of water in a subject's body and an embodiment of the configuration of a tip region thereof.

FIG. 6 is a diagram illustrating a configuration of a device 600 for measuring the amount of water in a subject's body and the configuration of a tip region 661 of the device 600 for measuring the amount of water in a subject's body. Configurations that are the same as the configurations described with reference to FIGS. 1A and 1B will be denoted by the same reference numerals, and description thereof will be omitted. Hereinbelow, differences from the embodiments described in conjunction with FIG. 1 will be described.

As illustrated in 6b of FIG. 6, the device 600 for measuring the amount of water in a subject's body can include, a protective member 651 that can have a thickness that is thin at a central position in the slide direction. When a tip side insertion part 120-2 slides in a direction indicated by an arrow 141a, the protective member 651 is bent outward at the central position in the slide direction, thereby releasing a force acting in the slide direction outward (refer to the right side on the drawing).

Forming the cross-sectional shape of the protective member 651 in such a manner to guide a bending direction prevents the protective member 651 from disturbing the slide operation of the tip side insertion part 120-2. Thus, a measurer can perform a pressing operation with a constant pressing force. Examples of a preferred material of the protective member 651 can include, but are not limited to, elastic members, (such as elastomers such as a silicone elastomer, polyurethane elastomer, or styrene elastomer), polyolefins (such as polyethylene), etc. Further, to give the protective member 651 an antifouling property, the protective member 651 may be coated with a fluorine resin having a trifluoromethyl group (—CF3) as a functional group or like coating.

The protective member 651 has no unevenness on the outer peripheral surface thereof. Therefore, even when dirt is adhered to the protective member 651, it is possible to wipe off the dirt more easily than the case in which a bellows-like elastic member is used as the protective member. As shown in FIGS. 6A and 6B, the protective member 651 is bent outward. However, the embodiments are not limited thereto, and the protective member may also be bent inward, as illustrated below.

Figure 7:
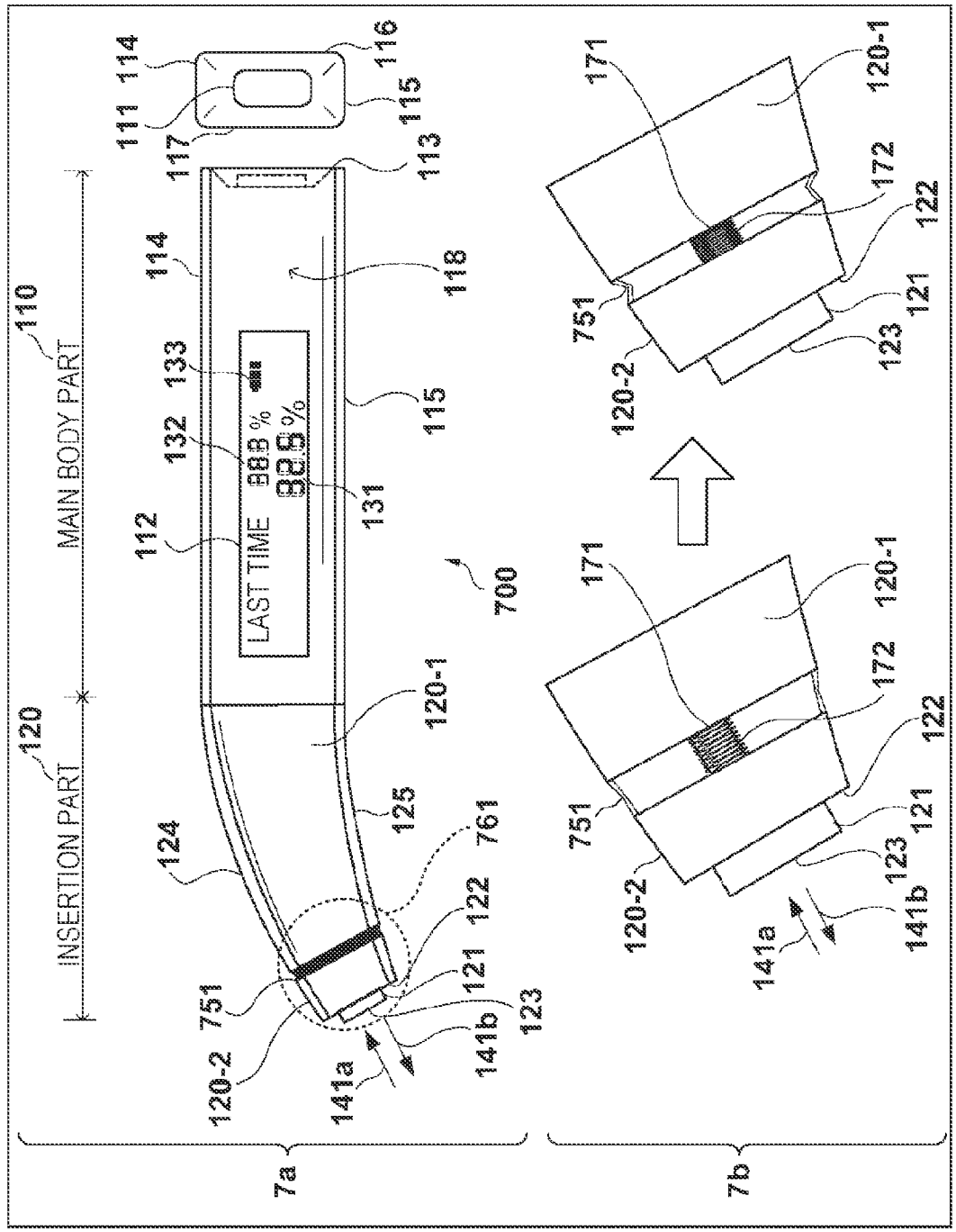
FIG. 7 is a diagram illustrating a configuration of an embodiment of a device for measuring the amount of water in a subject's body and an embodiment of the configuration of a tip region thereof.

FIG. 7 is a diagram illustrating an embodiment of a device 700 for measuring the amount of water in a subject's body and the configuration of a tip region 761 of the device 700 for measuring the amount of water in a subject's body. Configurations that are the same as the configurations described with reference to FIGS. 1A and 1B will be denoted by the same reference numerals, and description thereof will be omitted. Hereinbelow, the differences to the embodiments described in conjunction with FIGS. 1A and 1B will be described.

As illustrated in FIG. 7b, in the device 700 for measuring the amount of water in a subject's body, a protective member 751 has a thickness that is thin at a central position in the slide direction. When a tip side insertion part 120-2 slides in a direction indicated by an arrow 141a, the protective member 751 is bent inward at the central position in the slide direction, thereby releasing a force acting in the slide direction inward (refer to the right side on the drawing).

Forming the cross-sectional shape of the protective member 751 in such a manner to guide a bending direction prevents the protective member 751 from disturbing the slide operation of the tip side insertion part 120-2. Thus, a measurer can perform a pressing operation with a constant pressing force. Examples of preferred materials of the protective member 751 can include, but are not limited to, elastic members, such as elastomers (such as a silicone elastomer, polyurethane elastomer, or styrene elastomer), polyolefins (such as polyethylene), etc. Further, to give the protective member 751 an antifouling property, the protective member 751 may be coated with a fluorine resin having a trifluoromethyl group (—CF3) as a functional group or like coating.

The embodiments, described in conjunction with FIG. 7, also have the advantage of preventing interference with the armpit of a subject during measurement compared to the configuration that is bent outward as described in conjunction with FIG. 6.

In the embodiments described above, the outer peripheral surface of the base end side insertion part 120-1 and the outer peripheral surface of the tip side insertion part 120-2 are smoothly connected to each other by the protective member to thereby liquid-tightly cover the slide mechanism. However, the embodiments are not limited thereto.

For example, the base end side insertion part 120-1 and the sensor unit 121 may be directly and smoothly connected to each other by the protective member without providing the tip side insertion part.

Figure 8:
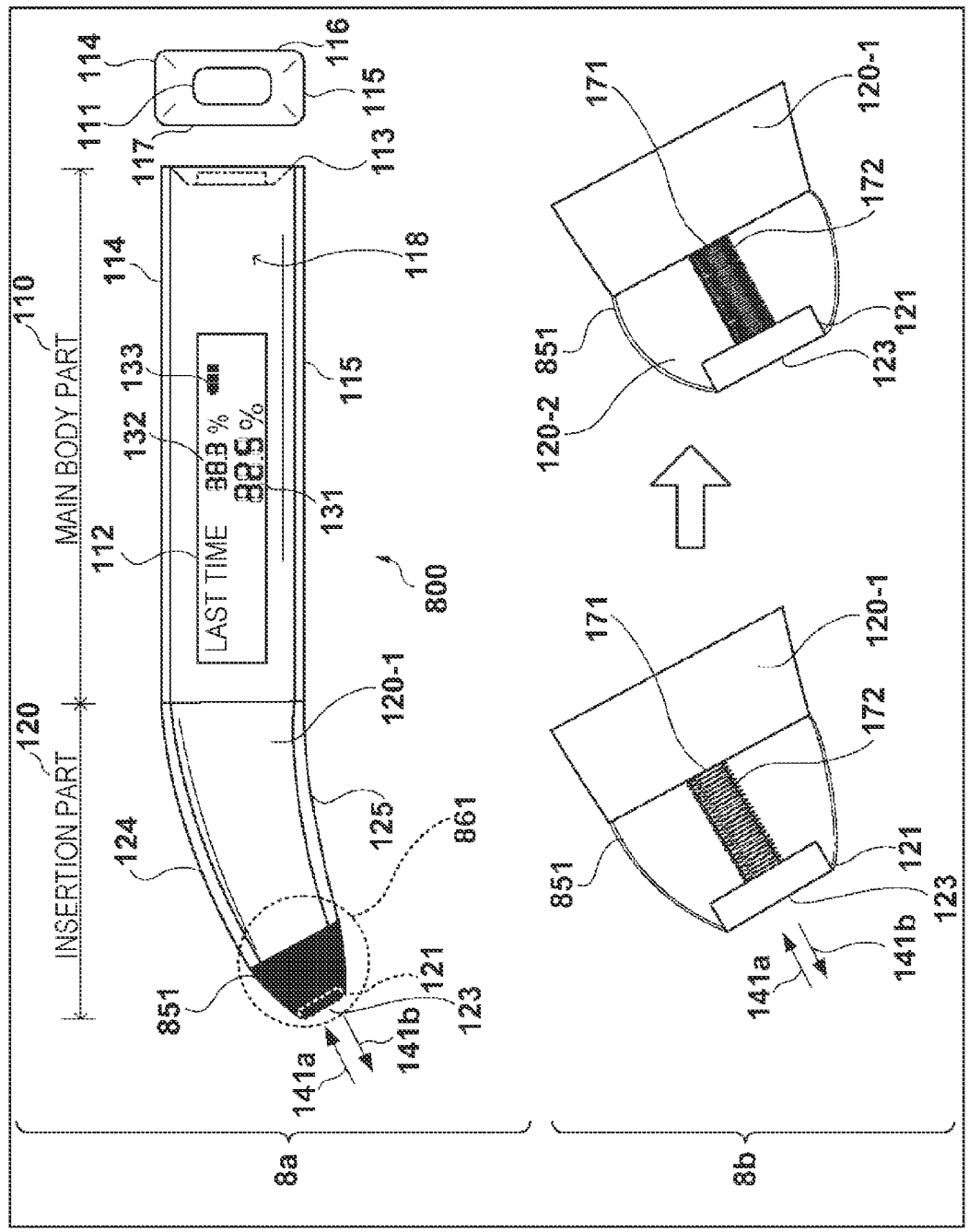
FIG. 8 is a diagram illustrating a configuration of an embodiment of a device for measuring the amount of water in a subject's body and a and the configuration of a tip region thereof.

FIG. 8 is a diagram illustrating a configuration, of a device 800, for measuring the amount of water in a subject's body and the configuration of a tip region 861 of the device 800 for measuring the amount of water in a subject's body. Elements that are the same as the configurations described with reference to FIGS. 1A and 1B will be denoted by the same reference numerals, and the description thereof will be omitted. Hereinbelow, differences to the embodiments described in conjunction with FIGS. 1A and 1B will be described hereinafter.

As illustrated in 8b of FIG. 8, in the device 800 for measuring the amount of water in a subject's body, a base end side insertion part 120-1 and the side surface of a sensor unit 121 are directly connected to each other by a protective member 851. When the sensor unit 121 slides in a direction indicated by an arrow 141a, the protective member 851 is curved outward (refer to the right side on the drawing). Examples of a preferred material of the protective member 851 can include, but are not limited to, elastic members, such as elastomers (such as a silicone elastomer, polyurethane elastomer, or styrene elastomer), polyolefins (such as polyethylene), etc. Further, to give the protective member 851 an antifouling property, the protective member 851 may be coated with a fluorine resin having a trifluoromethyl group (—CF3) as a functional group or like coating.

Directly connecting the sensor unit 121 and the base end side insertion part 120-1 to each other, in the manner shown in FIG. 8, eliminates a step or ridge between a tip surface 122 of the tip side insertion part 120-2 and the sensor unit 121. Therefore, even when dirt is adhered to the sensor unit 121, it is possible to wipe off the dirt more easily than the other embodiments.

In the embodiments described above, details of a method for connecting the protective member to the base end side insertion part and the tip side insertion part has not been particularly described. However, the base end side and tip end side insertion parts and the protective member desirably have configurations capable of preventing entrance of liquid through contact surfaces therebetween. Hereinbelow, details of the connection method will be described using the protective member 651 as an example.

Figure 9:
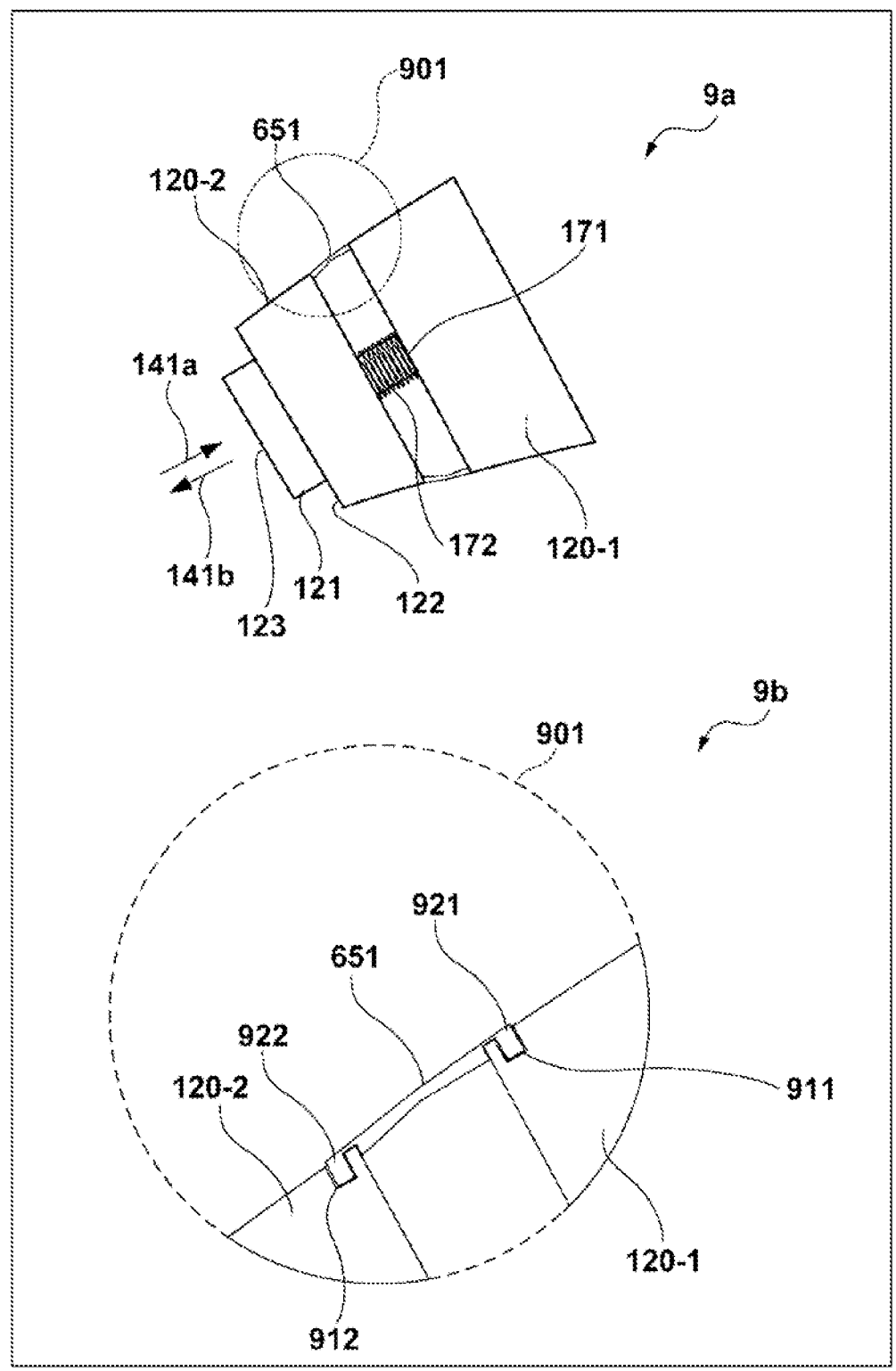
FIG. 9 is a diagram for explaining an embodiment of a method for connecting a protective member.

FIG. 9 is a diagram for explaining details of the method for connecting the protective member 651. FIG. 9a is the same as 6b FIG. 9b is an enlarged view of a region indicated by a dotted line 901 of 9a.

As illustrated in FIG. 9b, a groove 911 is formed on the outer peripheral surface of the base end side insertion part 120-1 over the whole circumference thereof. Further, a groove 912 is formed on the outer peripheral surface of the tip side insertion part 120-2 over the whole circumference thereof. Alternatively or additionally, projections 921 and 922 are formed on opposite ends of the protective member 651 in a direction substantially perpendicular to the slide direction. When the protective member 651 is connected to the base end side insertion part 120-1 and the tip side insertion part 120-2, the projections 921 and 922 are respectively fitted with the grooves 911 and 912.

Forming the grooves 911, 912 in the direction that is substantially perpendicular to a liquid entering direction in this manner makes it possible to reliably prevent entrance of liquid through a contact surface between the protective member 651 and the outer peripheral surface of the base end side insertion part 120-1 or a contact surface between the protective member 651 and the outer peripheral surface of the tip side insertion part 120-2.

In embodiments, a single groove is formed on each of the outer peripheral surface of the base end side insertion part 120-1 and the outer peripheral surface of the tip side insertion part 120-2, respectively. However, the embodiments are not limited thereto.

Figure 10:
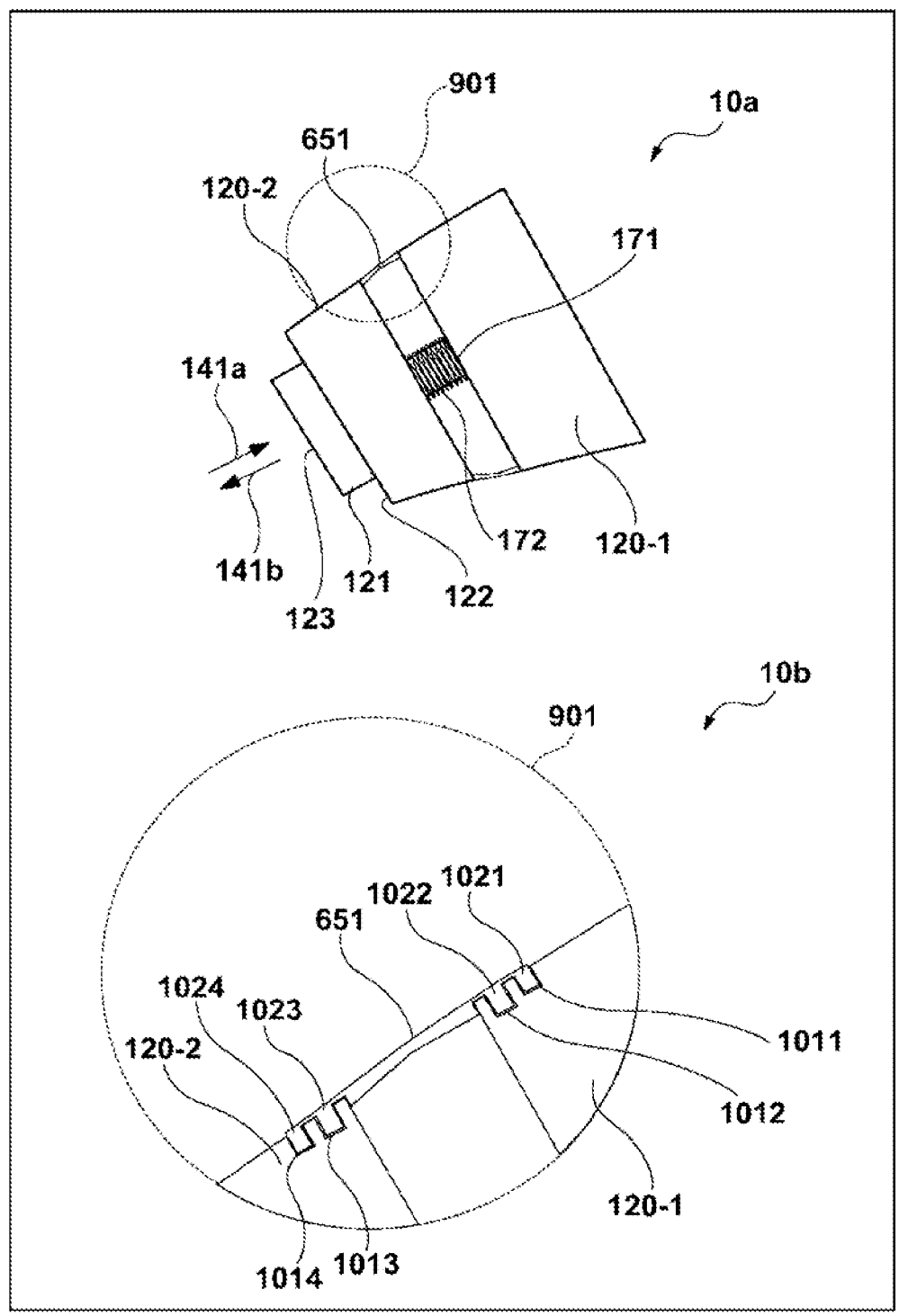
FIG. 10 is a diagram for explaining another embodiment of method for connecting the protective member.

FIG. 10 is a diagram for explaining another method for connecting the protective member 651. FIG. 10a is the same as FIG. 6b and FIG. 10b is an enlarged view of a region indicated by a dotted line 1001 of FIG. 10a.

As illustrated in FIG. 10b, two grooves (grooves 1011, 1012) are formed on the outer peripheral surface of the base end side insertion part 120-1 over the whole circumference thereof. Further, two grooves (grooves 1013, 1014) are formed on the outer peripheral surface of the tip side insertion part 120-2 over the whole circumference thereof.

On the other hand, two projections (projections 1021, 1022) can be formed on one end of the protective member 651 in a direction substantially perpendicular to the slide direction. Further, two projections (projections 1023, 1024) may be formed on the other end of the protective member 651 in the direction substantially perpendicular to the slide direction. When the protective member 651 is connected to the base end side insertion part 120-1 and the tip side insertion part 120-2, the projections 1021 to 1024 are respectively fitted with the grooves 1011 to 1014.

Forming the two grooves in each of the insertion parts in the direction that is substantially perpendicular to a liquid entering direction in this manner makes it possible to more reliably prevent entrance of liquid through a contact surface between the protective member 651 and the outer peripheral surface of the base end side insertion part 120-2 or a contact surface between the protective member 651 and the outer peripheral surface of the tip side insertion part 120-2.

In embodiments, configurations that emphasize improvement of the waterproof and antifouling properties have been described as the method for connecting the protective member to the base end side insertion part and the tip side insertion part. However, the embodiments are not limited thereto. A connection method that improves the waterproof and antifouling properties and also makes a wiping operation easy may be employed. Hereinbelow, details of a connection method of the present embodiment will be specifically described also taking the protective member 651 as an example.

Figure 11:
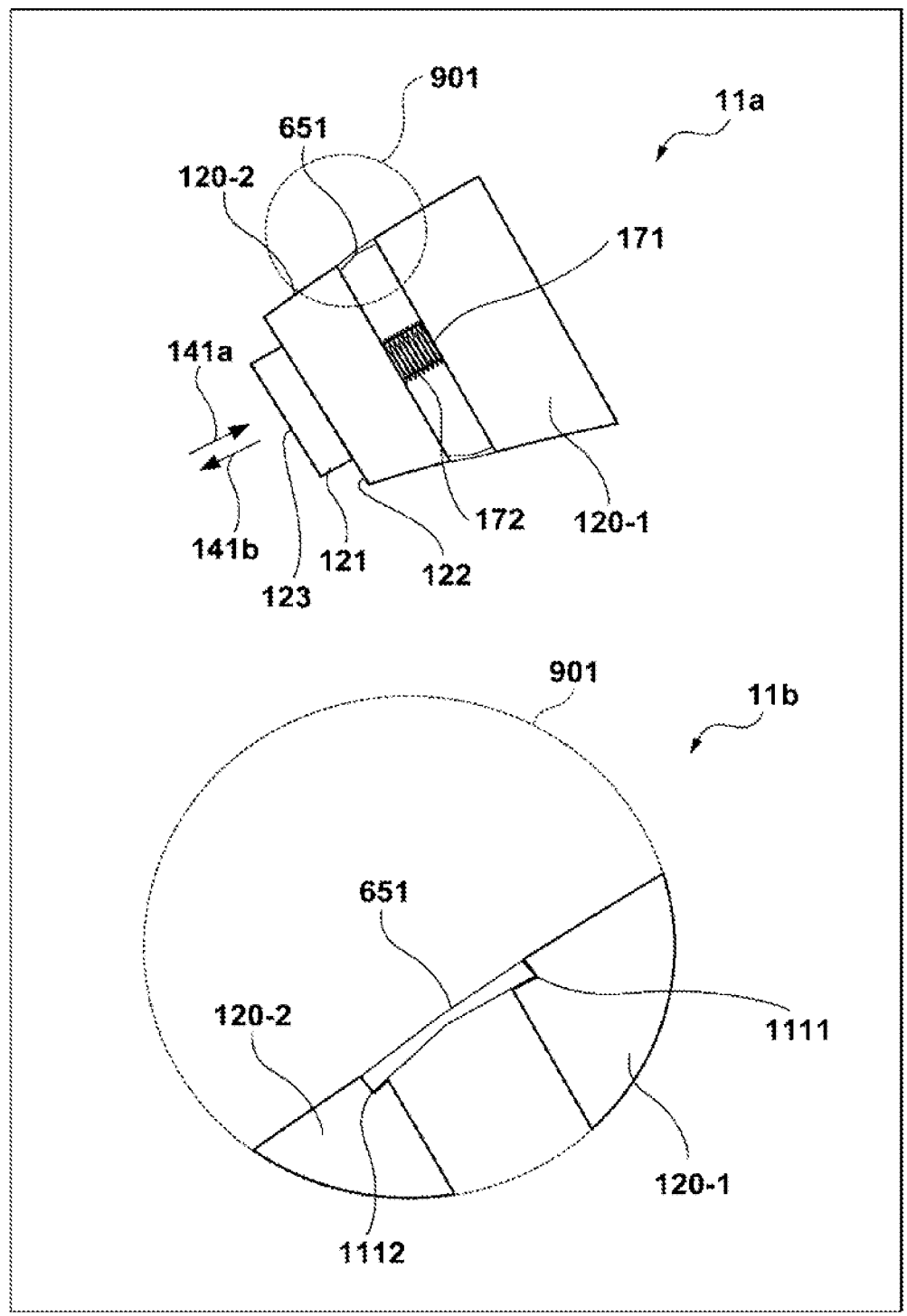
FIG. 11 is a diagram for explaining still another embodiment of method for connecting the protective member.

FIG. 11 is a diagram for explaining still another method for connecting the protective member 651. FIG. 11a is the same as FIG. 6b and FIG. 11b is an enlarged view of a region indicated by a dotted line 1101 of FIG. 11a.

As illustrated in FIG. 11b, a groove 1111 which has a depth corresponding to the thickness of the end of the protective member 651 is formed on the end of the outer peripheral surface of the base end side insertion part 120-1 over the whole circumference thereof. Further, a groove 1112 which has a depth corresponding to the thickness of the end of the protective member 651 is formed on the end of the outer peripheral surface of the tip side insertion part 120-12 over the whole circumference thereof.

Accordingly, when the protective member 651 is connected to the base end side insertion part 120-1 and the tip side insertion part 120-2, the ends of the protective member 651 are fitted with the grooves 1111 and 1112.

As a result, it is possible to reliably prevent entrance of liquid through a contact surface between the protective member 651 and the outer peripheral surface of the base end side insertion part 120-1 or a contact surface between the protective member 651 and the outer peripheral surface of the tip side insertion part 120-2. In addition, it is possible to completely eliminate steps, ridges, or edges between the outer peripheral surface of the base end side insertion part 120-1 and the protective member 651 and between the outer peripheral surface of the tip side insertion part 120-2 and the protective member 651, and thereby make a wiping operation by a measurer easier.

The embodiments are not limited to the above embodiments. Various changes and modifications can be made without departing from the spirit and scope of the invention. Therefore, the following claims are appended to disclose the scope of the invention.

The invention claimed is:

1. A device for measuring the amount of water in a subject's body comprising:
   a main body part formed in a linear shape; and
   an insertion part extending in a curved shape from one end of the main body part, the insertion part including:
   a tip side insertion part having a tip surface to which a sensor unit is fixed, wherein the sensor unit is brought into contact with a body surface of a subject to measure data regarding water in a subject's body,
   a base end side insertion part supporting the tip side insertion part through a slide mechanism, wherein the slide mechanism allows the tip side insertion part to slide in a direction substantially perpendicular to the tip surface, and a protective member liquid-tightly covering the slide mechanism between the tip side insertion part and the base end side insertion part, wherein the protective member smoothly connects a first outer peripheral surface of the tip side insertion part, wherein the first outer peripheral surface is a first outer most surface that faces radial outward on an exterior of the tip insertion part, and a second outer peripheral surface of the base end side insertion part to each other, wherein the second outer peripheral surface is a second outer most surface that faces radial outward on an exterior of the base end side insertion part;

wherein at least a first groove is formed on the first outer peripheral surface of the tip side insertion part in a first region to which the protective member is connected over the whole circumference, at least a second groove is formed on the second outer peripheral surface of the base end side insertion part in a second region to which the protective member is connected over the whole circumference, and projections formed on ends of the protective member are fitted with the first and second grooves when the protective member is connected.

2. The device for measuring the amount of water in a subject's body according to claim 1, wherein the protective member is made of one of an elastomer and a polyolefin.

3. The device for measuring the amount of water in a subject's body according to claim 1, wherein the first groove has a first depth that corresponds to the thickness of a first end of the protective member, wherein the second groove has a second depth that corresponds to the thickness of a second end of the protective member.

4. The device for measuring the amount of water in a subject's body according to claim 1, wherein the protective member extends and contracts in the slide direction.

5. The device for measuring the amount of water in a subject's body according to claim 1, wherein the sensor unit measures capacitance with a CR circuit.

6. The device for measuring the amount of water in a subject's body according to claim 1, wherein the protective member is bendable at a central position in the slide direction to release a force acting in the slide direction to a direction that differs from the slide direction.

7. The device for measuring the amount of water in a subject's body according to claim 6, wherein the protective member is coated with a flourine resin.

8. The device for measuring the amount of water in a subject's body according to claim 6, wherein the protective member eliminates a step or ridge between a tip surface and the sensor unit.

9. An insertion part of a device for measuring an amount of water in a subject's body, the insertion part comprising:
a tip side insertion part having a tip surface with a sensor unit, wherein the sensor unit is brought into contact with a body surface of the subject's body to measure data regarding water in the subject's body,
a base end side insertion part supporting the tip side insertion part through a slide mechanism, wherein the slide mechanism allows the tip side insertion part to slide in a direction substantially perpendicular to the tip surface, and
a protective member liquid-tightly covering the slide mechanism between the tip side insertion part and the base end side insertion part, wherein the protective member smoothly connects a first outer peripheral surface of the tip side insertion part, wherein the first outer peripheral surface is a first outer most surface that faces radial outward on an exterior of the tip insertion part, and a second outer peripheral surface of the base end side insertion part to each other, wherein the second outer peripheral surface is a second outer most surface that faces radial outward on an exterior of the base end side insertion part;

wherein a first groove having a first depth corresponding to the first thickness of a first end of the protective member is formed on the first outer peripheral surface of the tip side insertion part in a first region to which the protective member is connected over a whole circumference, wherein a second groove having a second depth corresponding to the second thickness of a second end of the protective member is formed on the second outer peripheral surface of the base end side insertion part in a second region to which the protective member is connected over the whole circumference, and the first and second ends of the protective member are fitted with the first and second grooves when the protective member is connected.

10. The insertion part according to claim 9, wherein the protective member is made of one of an elastomer and a polyolefin.

11. The insertion part according to claim 10, wherein the one of the elastomer and the polyolefin is one of a silicone elastomer, a polyurethane elastomer, a styrene elastomer, and polyethylene.

12. The insertion part according to claim 9, wherein the sensor unit measures capacitance with a CR circuit.

13. The insertion part according to claim 9, wherein the protective member is coated with a fluorine resin.

14. The insertion part according to claim 9, wherein the protective member eliminates a step or ridge between a tip surface and the sensor unit.

15. The insertion part according to claim 9, wherein the protective member bends one of substantially perpendicularly outward or substantially perpendicularly inward relative to the slide motion.

16. The insertion part according to claim 9, further comprising:
a sensor unit to measure an oscillatory frequency of an output signal;
a processor to:
detect an instruction to start the measurement;
receive the measured oscillatory frequency;
calculate the amount of water in a subject's body based on the measured oscillatory frequency; and
determine, based on the calculated amount of water in a subject's body, whether the subject is dehydrated.

17. The insertion part according to claim 16, further comprising a display to display the amount of water in a subject's body.

18. A method for acquiring a measurement of an amount of water in a subject's body using a device, the method comprising:
sliding a sensor unit fixed to a tip surface, of a tip side insertion part, into contact with a body surface of the subject's body, wherein a base end side insertion part supports the tip side insertion part through a slide mechanism, wherein the slide mechanism allows the tip side insertion part to slide in a direction substantially perpendicular to the tip surface, and wherein a protective member liquid-tightly covers the slide mechanism between the tip side insertion part and the base end side insertion part, wherein the protective member smoothly connects a first outer peripheral surface of the tip side insertion part, wherein the first outer peripheral surface is a first outer most surface that faces radial outward on an exterior of the tip insertion part, and a second outer peripheral surface of the base end side insertion part to each other, wherein the second outer peripheral surface is a second outer most surface that faces radial outward on an exterior of the base end side insertion part;

a processor detecting an instruction to start the measurement;

the sensor unit measuring an oscillatory frequency of an output signal;

the processor receiving the measured oscillatory frequency;

the processor calculating the amount of water in a subject's body based on the measured oscillatory frequency;

the processor determining, based on the calculated amount of water in a subject's body, whether the subject is dehydrated; and displaying the amount of water in a subject's body on a display of the device.

19. The method according to claim 18, further comprising the protective member preventing the intrusion of water into the device.

20. The device for measuring the amount of water in a subject's body according to claim 2, wherein the one of the elastomer and the polyolefin is one of a silicone elastomer, a polyurethane elastomer, a styrene elastomer, and polyethylene.

* * * * *